US010096094B2

United States Patent
Carlson et al.

(10) Patent No.: US 10,096,094 B2
(45) Date of Patent: *Oct. 9, 2018

(54) ALIGNMENT OF MIXED-MODALITY DATA SETS FOR REDUCTION AND REMOVAL OF IMAGING ARTIFACTS

(71) Applicant: Dental Imaging Technologies Corporation, Hatfield, PA (US)

(72) Inventors: Bradley S. Carlson, Doylestown, PA (US); Edward Marandola, Gwynedd, PA (US); David A. Sebok, Eagleville, PA (US); Uwe Mundry, Landrum, SC (US)

(73) Assignee: Dental Imaging Technologies Corporation, Hatfield, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/854,570

(22) Filed: Dec. 26, 2017

(65) Prior Publication Data

US 2018/0137608 A1 May 17, 2018

Related U.S. Application Data

(63) Continuation of application No. 15/595,826, filed on May 15, 2017, now Pat. No. 9,886,748, which is a
(Continued)

(51) Int. Cl.
*G06K 9/00* (2006.01)
*G06T 5/00* (2006.01)

(52) U.S. Cl.
CPC .... *G06T 5/005* (2013.01); *G06T 2207/10081* (2013.01); *G06T 2207/10116* (2013.01)

(58) Field of Classification Search
CPC ................. G06T 11/008; G06T 19/20; G06T 2207/10084; G06T 2207/30036;
(Continued)

(56) References Cited

U.S. PATENT DOCUMENTS

| 4,941,164 A | 7/1990 | Schuller et al. |
| 6,068,482 A | 5/2000 | Snow |

(Continued)

FOREIGN PATENT DOCUMENTS

| JP | H10143652 A | 5/1998 |
| JP | 2009078133 | 4/2009 |

(Continued)

OTHER PUBLICATIONS

Nkenke, E. et al., "Fusion of computed tomography data and optical 3D images of the dentition for streak artefact correction in the simulation of orthognatic surgery," Dentomaxillofacial Radiology (2004) 33:226-232.

(Continued)

*Primary Examiner* — Tom Y Lu
(74) *Attorney, Agent, or Firm* — Michael Best & Friedrich LLP

(57) ABSTRACT

Methods and systems are described for removing reflective artifacts from an imaging model. An x-ray detector captures x-ray images that include a structure and an imaging device captures a surface scan of the same structure. An image processor constructs a three-dimensional CT model of the structure from the x-ray images and constructs a three-dimensional surface model of the structure from the surface scan. The image processor is configured to resize and orient the surface model and/or the CT model so that they are the same scale and orientation, overlay the surface model onto the CT model, and detect data points in the combined data set that extend beyond a surface of the structure in the surface model. The detected data points represent artifacts in the CT model and are adjusted by interpolation to produce an artifact-reduced CT model.

3 Claims, 11 Drawing Sheets

Related U.S. Application Data continuation of application No. 14/714,603, filed on May 18, 2015, now Pat. No. 9,684,952, which is a continuation-in-part of application No. 13/090,786, filed on Apr. 20, 2011, now Pat. No. 9,036,881.

(60) Provisional application No. 61/326,031, filed on Apr. 20, 2010.

(58) Field of Classification Search
CPC ............ G06T 2219/2016; G06T 5/005; G06T 2207/10081; G06T 2211/40; G06T 2219/2004; G06T 2219/2021; A61B 5/0064; A61B 6/032; A61B 6/14; A61B 6/4085; A61B 6/4435; A61B 6/5247
See application file for complete search history.

(56) References Cited

U.S. PATENT DOCUMENTS

| | | | |
|---|---|---|---|
| 6,152,731 | A | 11/2000 | Jordan et al. |
| 6,671,529 | B2 | 12/2003 | Claure et al. |
| 6,845,175 | B2 | 1/2005 | Kopelman et al. |
| 7,200,642 | B2 | 4/2007 | Hultgren et al. |
| 7,574,025 | B2 | 8/2009 | Feldman |
| 7,991,243 | B2 | 8/2011 | Bal et al. |
| 8,170,327 | B2 | 5/2012 | Glor et al. |
| 8,199,988 | B2 | 6/2012 | Marshall et al. |
| 8,364,301 | B2 | 1/2013 | Schmitt |
| 9,036,881 | B2 * | 5/2015 | Carlson ................ A61B 5/0064 382/131 |
| 2004/0197727 | A1 | 10/2004 | Sachdeva et al. |
| 2007/0190481 | A1 | 8/2007 | Schmitt |
| 2007/0207441 | A1 | 9/2007 | Lauren |
| 2008/0228303 | A1 | 9/2008 | Schmitt |
| 2009/0220916 | A1 | 9/2009 | Fisker et al. |
| 2009/0238334 | A1 | 9/2009 | Brahme et al. |
| 2009/0295795 | A1 | 12/2009 | Feldman |
| 2009/0316966 | A1 | 12/2009 | Marshall et al. |
| 2009/0325127 | A1 | 12/2009 | Kusch et al. |
| 2010/0124367 | A1 | 5/2010 | Cizek |
| 2011/0268327 | A1 | 11/2011 | Getto et al. |

FOREIGN PATENT DOCUMENTS

| | | |
|---|---|---|
| JP | 2009-233294 | 10/2009 |
| JP | 2009297392 A | 12/2009 |
| JP | 2010-068832 | 4/2010 |
| WO | 2004098379 | 11/2004 |
| WO | 2008083874 | 7/2008 |
| WO | 2009063088 A2 | 5/2009 |

OTHER PUBLICATIONS

First Office Action from the State Intellectual Property Office of the People's Republic of China for Application No. 201180020294.9 dated Aug. 1, 2014 (22 pages).

English Translation of Second Notice of Preliminary Rejection from the Korean Intellectual Property Office for Application No. 10-2012-7030194 dated Aug. 29, 2014 (4 pages).

English Translation of Final Decision of Rejection from the Japanese Intellectual Property Office for Application No. 2013-506270 dated Feb. 25, 2015 (3 pages).

Notice of Preliminary Rejection with English translation from the Korean Intellectual Property Office for Application No. 10-2014-7033499 dated Jul. 5, 2016 (13 pages).

Office Action with English translation from the Japanese Patent Office for Application No. 2013-506270 dated Jun. 2, 2016 (4 pages).

Extended European Search Report from the European Patent Office for Application No. 11772629.9 dated May 23, 2017 (7 pages).

* cited by examiner

ALIGNMENT OF MIXED-MODALITY DATA SETS FOR REDUCTION AND REMOVAL OF IMAGING ARTIFACTS

RELATED APPLICATIONS

This patent application is a continuation of U.S. patent application Ser. No. 15/595,826, filed May 15, 2017, and entitled "ALIGNMENT OF MIXED-MODALITY DATA SETS FOR REDUCTION AND REMOVAL OF IMAGING ARTIFACTS," which is a continuation of U.S. patent application Ser. No. 14/714,603, filed on May 18, 2015, and entitled "ALIGNMENT OF MIXED-MODALITY DATA SETS FOR REDUCTION AND REMOVAL OF IMAGING ARTIFACTS," which is a continuation-in-part of U.S. patent application Ser. No. 13/090,786, filed on Apr. 20, 2011 and entitled "REDUCTION AND REMOVAL OF ARTIFACTS FROM A THREE-DIMENSIONAL DENTAL X-RAY DATA SET USING SURFACE SCAN INFORMATION," which claims priority to U.S. Provisional Patent Application No. 61/326,031 filed on Apr. 20, 2010, the entire contents of all of which are herein incorporated by reference.

BACKGROUND

The present invention relates to dental imaging technology. More specifically, the present invention relates to reconstructing a three-dimensional image of a patient's teeth using both x-ray and surface scanning technology.

X-ray technology can be used to generate a three-dimensional, digital representation of a subject using computed tomography (CT). However, metal and other objects can reflect x-rays that would otherwise penetrate through human tissue and be detected by the x-ray detector. This reflection can cause unwanted artifacts to appear in the captured data set. This effect is particularly prevalent in dental imaging where foreign substances such as metal fillings or braces are often installed in the patient's mouth.

There are some prior systems in which artifacts are removed from x-ray data by, simply stated, "combining" x-ray and non-x-ray data. However, as best known by the inventors, in addition to removing or reducing artifacts, such systems also remove significant amounts of desired image data.

U.S. Publication No. 2010/0124367 has suggested that artifacts can be removed from x-ray data by the "fusion of the x-ray data set with an optical image of the jaw, which is completely free of metal artifacts . . . ." However, details regarding how the artifacts would be removed are not provided and the "fusion" disclosed in the '367 publication uses a pre-positioning technique that requires identifying registration points on a screen or other manual means prior to combining the data. While this pre-positioning makes the task of combining the two data sets substantially easier than a completely automatic method, the method requires manual intervention. That is, the x-ray technician, dentist, or other dental professional must manually manipulate the images on a screen.

U.S. Pat. No. 6,671,529 describes a method of creating a composite skull model by combining three-dimensional CT data and laser surface scans of a patient's teeth. In the '529 patent, the teeth are completely removed from the CT model and replaced with only the surface scan data of the patient's teeth.

U.S. Pat. No. 7,574,025 describes a method of removing artifacts from a three-dimensional model (such as CT or MRI) by a negative impression template of the patient's teeth. In the '025 patent, a negative impression template is cast of the patient's teeth. A first model is generated while the negative impression template is placed in the patient's mouth. A second model is generated of only the negative impression template using the same imaging technology as the first. Voxels from the first digital image are substituted for corresponding voxels from the second digital image to create a model of the patient's teeth without artifacts.

SUMMARY

It would be useful to have an improved method and system of removing artifacts from x-ray data that did not remove significant portions of desired CT image data, substitute data from multiple x-rays, or require manual pre-positioning of the data sets.

In some embodiments, the invention provides a system for generating a three-dimensional, digital representation including a patient's teeth using both CT and surface scanning data. The system includes an x-ray source and an x-ray detector that are used to capture several x-ray images. The images are transmitted to an image processing system where they are used to construct a three-dimensional CT model of the patient's teeth. The system also includes a surface scanner (such as a laser or structured light scanning system) that captures data representing the shape and texture of the surface of the patient's teeth. The surface data is also transmitted to the image processing system where it is used to construct a three-dimensional model of the surface of the patient's teeth. The image processing system then resizes and orients the surface model and the CT model so that the two models are of the same scale and orientation.

In some embodiments, the surface model is then overlaid onto the CT model. This is achieved without requiring manual intervention. The system of this embodiment then detects artifacts in the CT model by detecting any data points in the CT model that extend beyond the overlaid surface model. Data points extending beyond the surface model are considered to be artifacts and the image processing system removes the artifact data points from the CT model. In other embodiments, any data points in the CT model that extend beyond the surface model are processed to determine whether they are artifacts. Processed data points that are identified as artifacts are then removed from the CT model. In some embodiments, after the artifact data points are identified and removed from the CT model, the overlaid surface data is then removed leaving only the three-dimensional CT model.

In some embodiments, the surface model is forward projected to create projection data in the same two-dimensional (2D) format as the CT projection data. The forward projected data is combined with the CT projection data to identify regions of metal and teeth and allow the CT reconstruction to remove the effects of metal from the reconstructed CT images. Again, this is achieved without requiring manual pre-positioning of the two sets of data with respect to one another.

In another embodiment, the invention provides a method for removing reflective artifacts from an imaging model of a patient's teeth. A first volumetric model and a second volumetric model of the patient's teeth are accessed from a computer-readable memory. The orientation and scale of at least one of the two models is repeatedly and automatically adjusted until an optimized orientation and scale is determined that correlates the first volumetric model and the second volumetric model. The second volumetric model is then overlaid onto the first volumetric model. Any data points in the first volumetric model that extend beyond a surface of the patient's teeth in the second volumetric model are detected and removed to create an artifact-reduced volumetric model.

In yet another embodiment, the invention provides a system for removing reflective artifacts from an imaging model of a patient's teeth. The system includes an x-ray source, an x-ray detector that captures x-ray images, a surface scanner that captures a surface scan of the patient's teeth, and an imaging processing system. The image processing system constructs a three-dimensional CT model of the patient's teeth from the x-ray images and constructs a three-dimensional surface model of the patient's teeth from the surface scan. The image processor is also configured to repeatedly and automatically adjust an orientation and a scale of at least one of the two volumetric models until an optimized orientation and scale are determined that correlates the first volumetric model and the second volumetric model. The second volumetric model is then overlaid onto the first volumetric model. Any points in the first volumetric model that extend beyond a surface of the patient's teeth in the second volumetric model are detected and removed to create an artifact-reduced volumetric model.

In still another embodiment, the invention provides a method of automatically aligning a first volumetric model of a patient's teeth and a second volumetric model of the same patient's teeth by repeating a series of acts. The repeated acts include evaluating an alignment of the first volumetric model and the second volumetric model, adjusting a variable of the first volumetric model or the second volumetric model (the variable being randomly selected from a group consisting of a yaw, a pitch, a roll, and a scale), evaluating an alignment of the first volumetric model and the second volumetric model after adjusting the variable, accepting the adjustment of the variable if the alignment of the first volumetric model and the second volumetric model is improved after the adjustment of the variable, generating a random threshold number, accepting the adjustment of the variable if the alignment of the first volumetric model and the second volumetric model is not improved after the adjustment of the variable and a calculated acceptance probability exceeds the random threshold number, rejecting the adjustment of the variable if the alignment of the first volumetric model and the second volumetric model is not improved after the adjustment of the variable and the calculated acceptance probability does not exceed the threshold number, and adjusting a probability variable used to calculate the acceptance probability, wherein adjusting the probability variable reduces the likelihood that the calculated acceptance probability will exceed the random threshold number on each subsequent repeat iteration.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
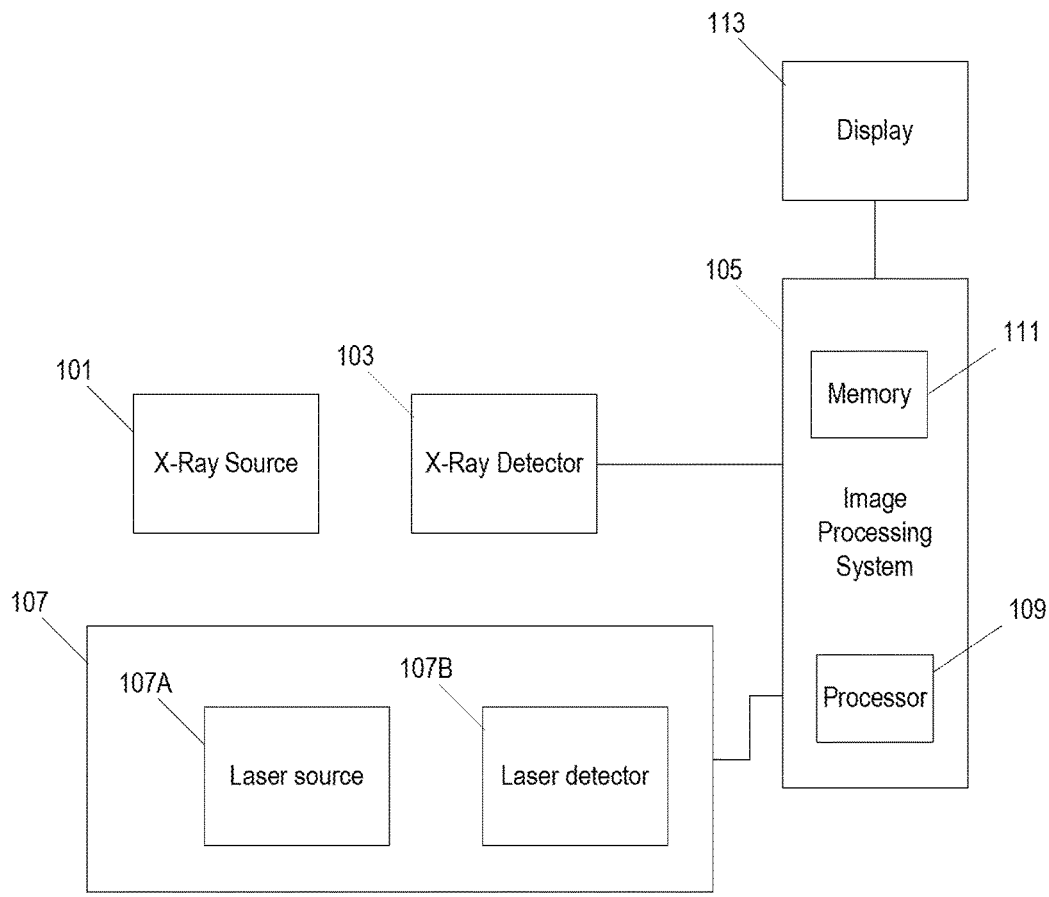
FIG. 1A is a block diagram illustrating the components of the imaging system according to one embodiment of the invention.

FIG. 1A is a block diagram illustrating the components of a system for removing artifacts from a three-dimensional digital CT model of a patient's teeth. The system can also be used to create three-dimensional digital models of the patient's jaw and other facial bones and tissue. The system includes an x-ray source 101 and an x-ray detector 103. The x-ray source 101 is positioned to project x-rays toward a patient's teeth. The x-ray detector 103 is positioned on the opposite side of the patient's teeth—either inside the patient's oral cavity or on the opposite side of the patient's head. The x-rays from the x-ray source 101 are attenuated differently by the patient's tissue and are detected by the x-ray detector 103.

Figure 1B:
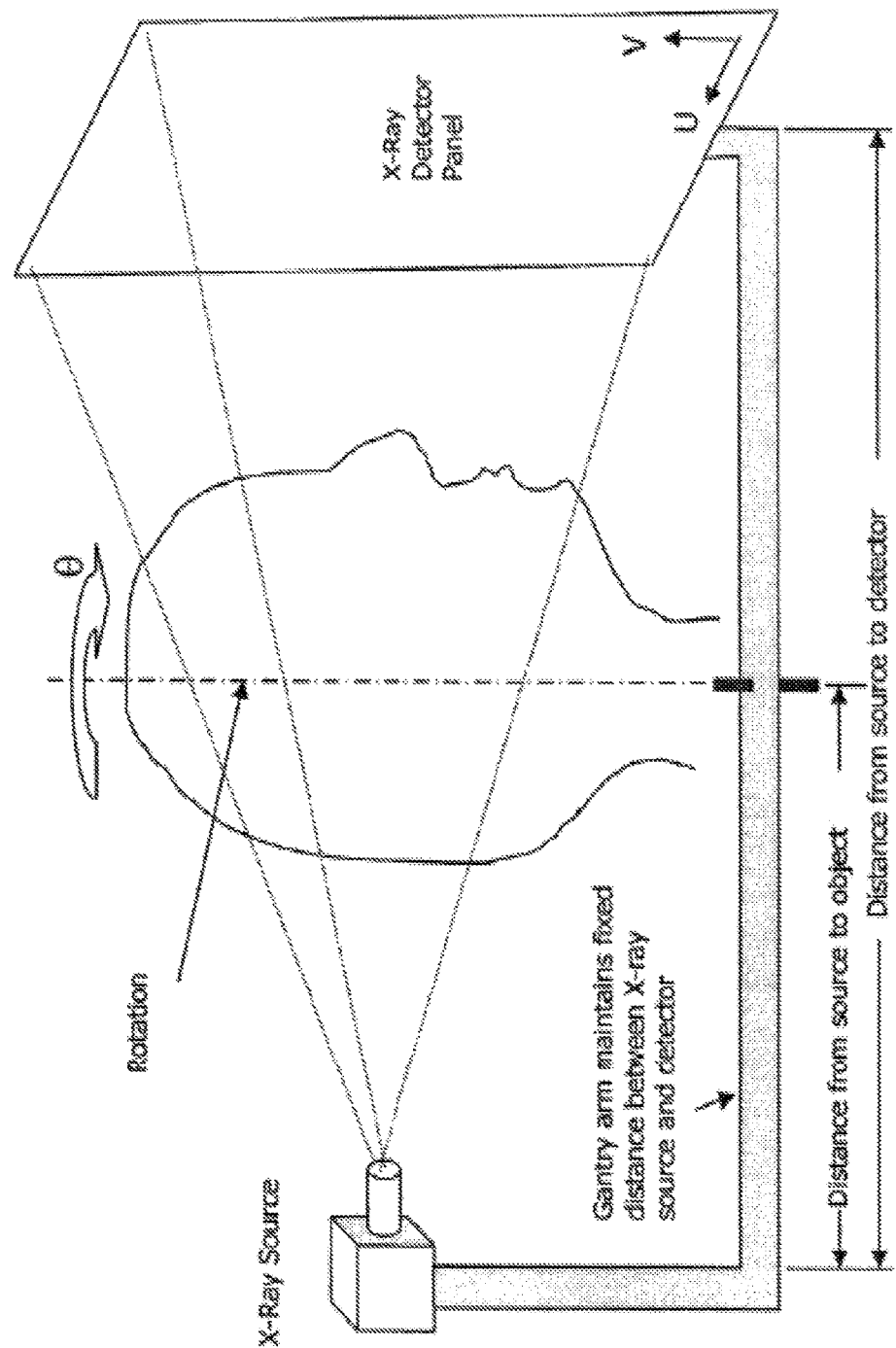
FIG. 1B is a diagram of a cone-beam CT scanning system used in the system of FIG. 1A.

The x-ray detector 103 is connected to an image processing system 105. The data captured by the x-ray detector 103 is used by the image processing system to generate a three-dimensional CT model of the patient's teeth. As such, in one embodiment, the x-ray source 101 and the x-ray detector 103 are part of a cone-beam, scanning CT system that rotates around the patient's head to collect x-ray image data as illustrated in FIG. 1B. An example of one such scanning system is described in U.S. application Ser. No. 12/700,028 filed on Feb. 4, 2010, the entire contents of which are incorporated herein by reference. The '028 application relates to motion correction, but the imaging components—sensor and source mounted on a rotatable C-arm, are applicable to the techniques described herein.

The system illustrated in FIG. 1A also includes a surface scanning imaging system 107. The surface scanning system 107 captures data relating to the surface texture, size, and geometry of the patient's teeth. The captured surface data is then transmitted to the image processing system 105 where it is used to generate a three-dimensional surface model of the patient's teeth. In some embodiments, the surface scanning imaging system includes a laser transceiver system such as one including a laser source 107A and a laser sensor or digital camera 107B. The laser source scans a laser line across the surface of the patient's tooth. The sensor or camera captures images of the projected line. The image processing system 105 analyzes how the shape of the laser line from the perspective of the sensor or camera changes as it is scanned across the patient's tooth. This data is then used to generate the three-dimensional surface model of the patient's teeth.

The image processing system 105 in FIG. 1A includes a processor 109 for executing computer instructions and a memory 111 for storing the instructions and data transmitted from the x-ray detector 103 and the surface scanning system 107. In some embodiments, the image processing system includes one or more desktop computers running image processing software. In other embodiments, the image processing system 105 is a device designed specifically for processing image data received from the x-ray detector 103 and the surface scanning system 107. Data captured by the x-ray detector 103 and the surface scanning imaging system 107 as well as processed volumetric data is displayed on a display 113.

Figure 2:
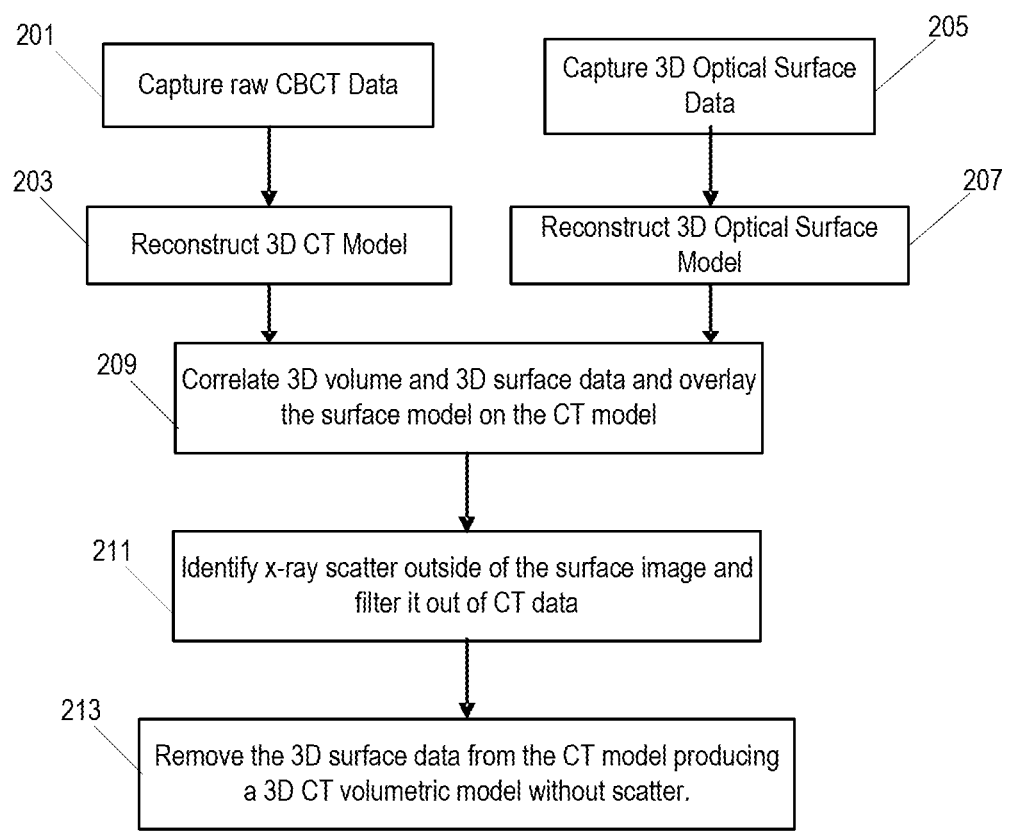
FIG. 2 is a flowchart showing the method of using the system of FIG. 1A to remove artifacts from a CT model.

FIG. 2 is a flowchart illustrating one method for how the system of FIG. 1A can be used to generate to a CT model of a patient's teeth and remove artifacts from a CT model of the patient's teeth. The system begins by capturing cone-beam CT (CBCT) image data of the patient's teeth (step 201). This is done by rotating the x-ray source 101 and the x-ray detector 103 around the patient's head to collect several x-ray images of the patient's teeth. The captured data is then used to generate a three-dimensional CT model of the patient's teeth (step 203). The surface scanning system 107 is used to capture optical surface data (step 205), which the image processing system 105 then uses to generate a three-dimensional surface model of the patient's teeth (step 207). In various embodiments, the surface data can be captured before or after the CT image is captured. Similarly, the CT data can be processed by the image processing system (step 203) before or after the surface data is captured by the surface scanning system 107 (step 205).

After both the CT model and the surface model have been generated, the image processing system 105 correlates the three-dimensional CT volume model and the three-dimensional optical surface model to determine a proper scale and orientation of the two models. The surface model is overlaid onto the CT model to generate a combined data set (step 209). In some embodiments, the system is calibrated such that the captured data includes registration information indicating the location and perspective from which the data was captured. In such embodiments, the proper scale and orientation of the two models is determined by matching the registration information from the CT model to the corresponding registration information from the surface model.

In other embodiments, the image processing system 105 uses surface matching algorithms to identify corresponding physical structures in both of the models. The identification of corresponding structures can be achieved, for example, by the identification of three or more anatomical landmarks that appear in both of the two models and then rotating, translating, and scaling one model until the differences between these landmarks is minimized within a predetermined tolerance. Alternatively, the entire surface in the two models can be matched by scaling, rotation, and translation through various well-known optimization techniques such as simulated annealing. A specific mechanism for determining an optimized orientation and scale of the two models based on the principle of simulated annealing is discussed in further detail below. A number of features in the two models can be characterized in each and correlated to determine the best match of the surfaces. The image processing system 105 sizes and orients the models according to the matching structures.

In some embodiments, the overlay process can be executed by overlaying the entire surface model onto the entire CT model. The image processing system 105 can also include various functions that segment the CT model into sub-volumes. The sub-volume functions can be used to isolate a single tooth from the CT model. In FIGS. 5-8, artifacts caused by x-ray reflective materials (such as metal filings) are removed from the CT model by overlaying data from the surface model onto sub-volumes of the CT model one tooth at a time.

Figure 5:
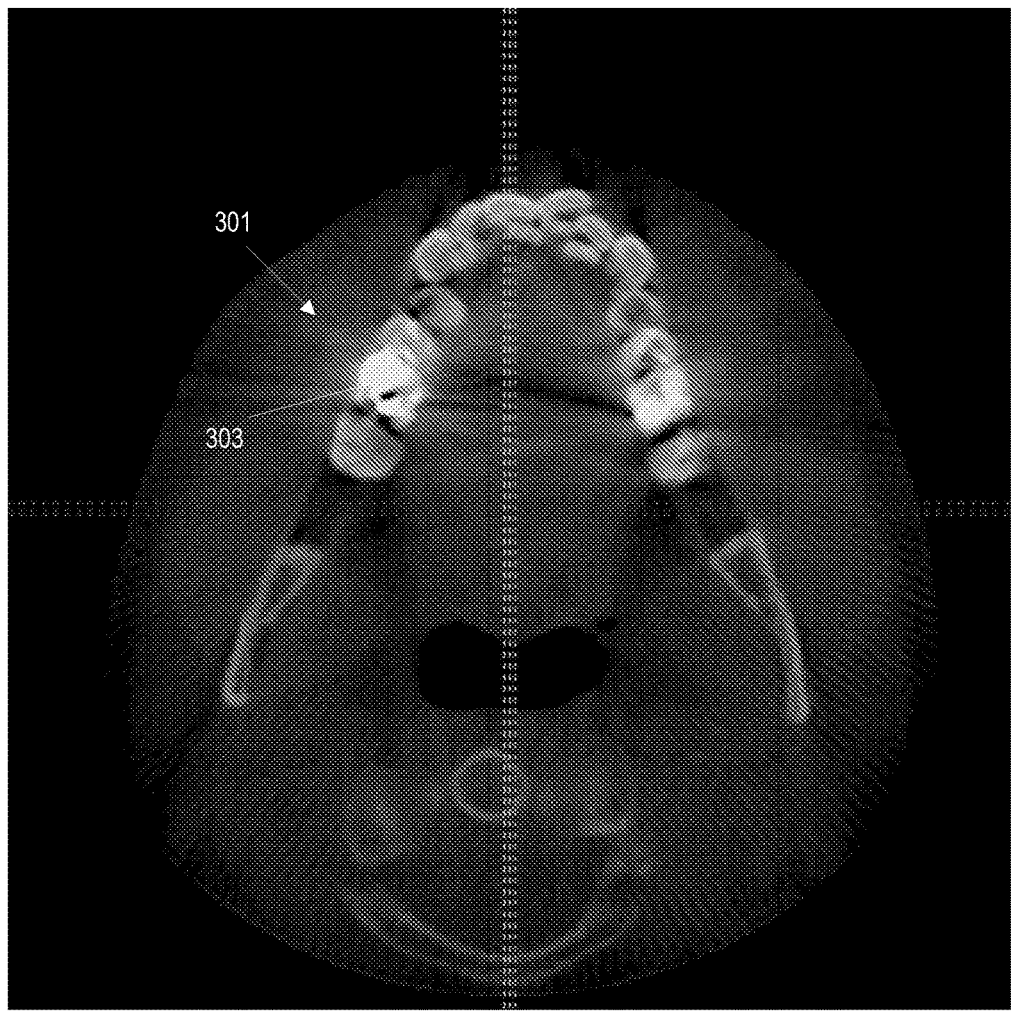
FIG. 5 is an image of a slice of the CT data captured by the x-ray detector of FIG. 1A.
Figure 6:
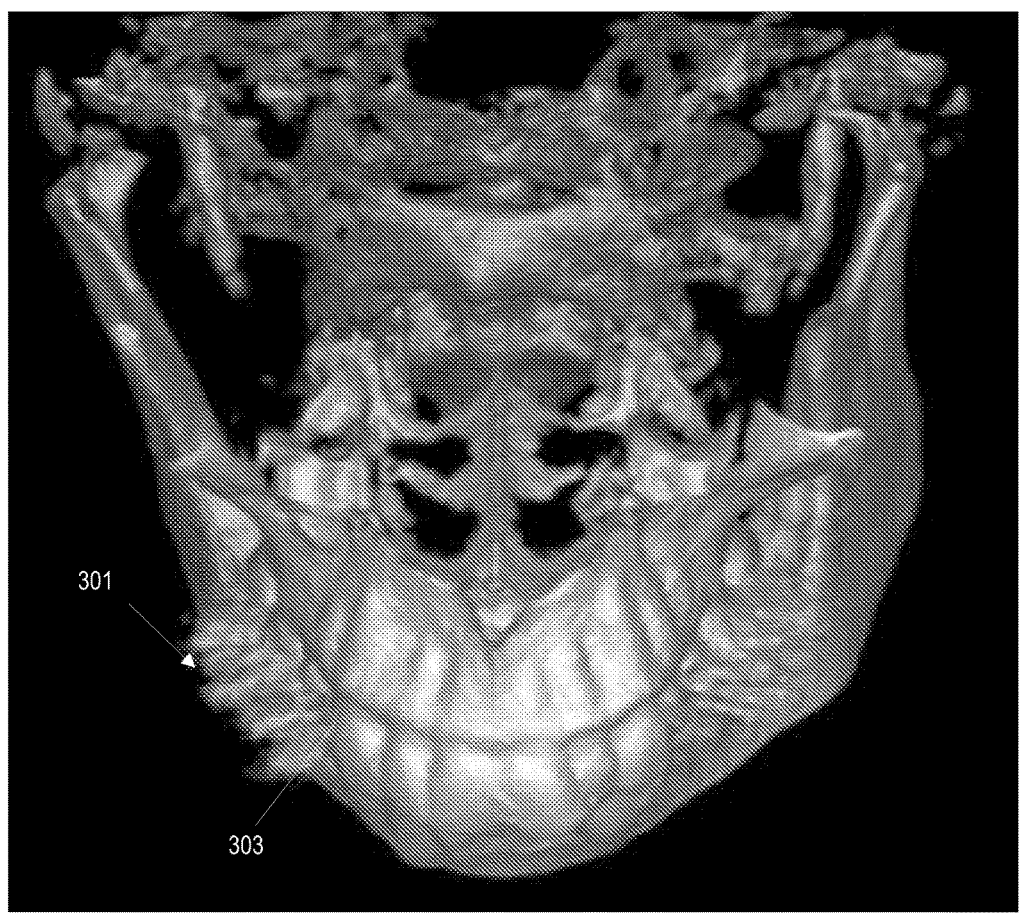
FIG. 6 is a perspective view of an unfiltered CT model of a patient's teeth and jaw with imaging artifacts.
Figure 7:
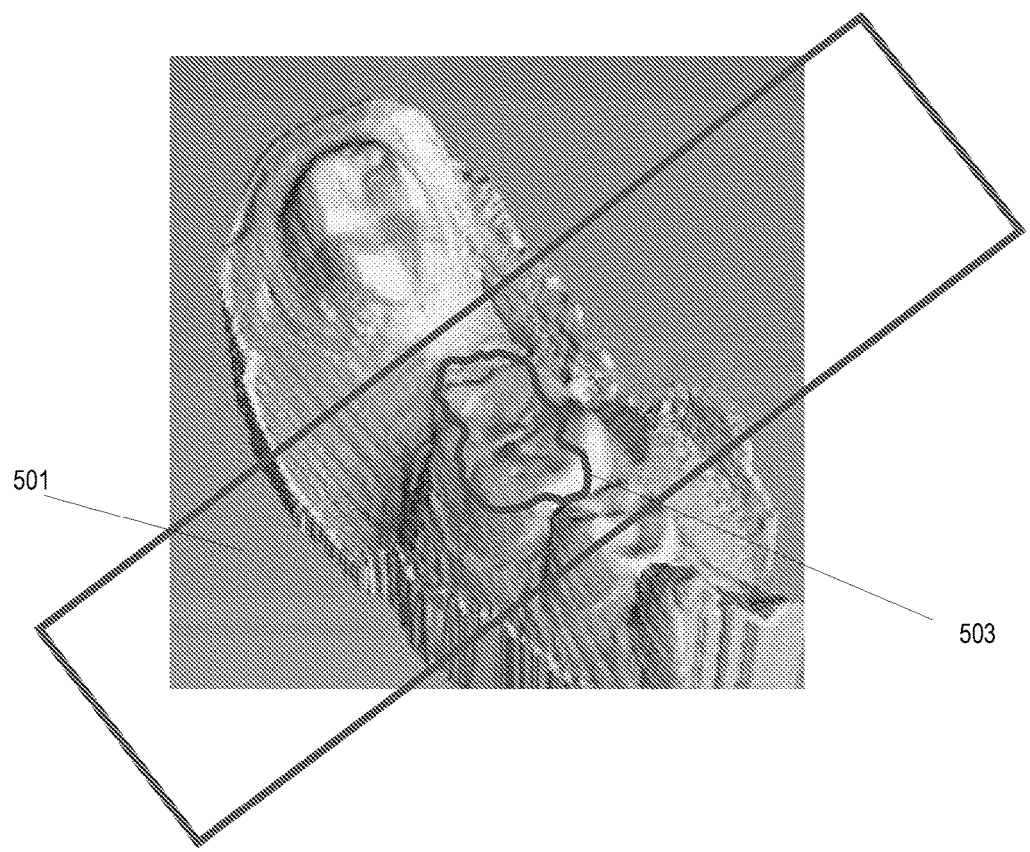
FIG. 7 is an overhead view of a surface model of a patient's teeth captured by the surface scanner of FIG. 1A.
Figure 8:
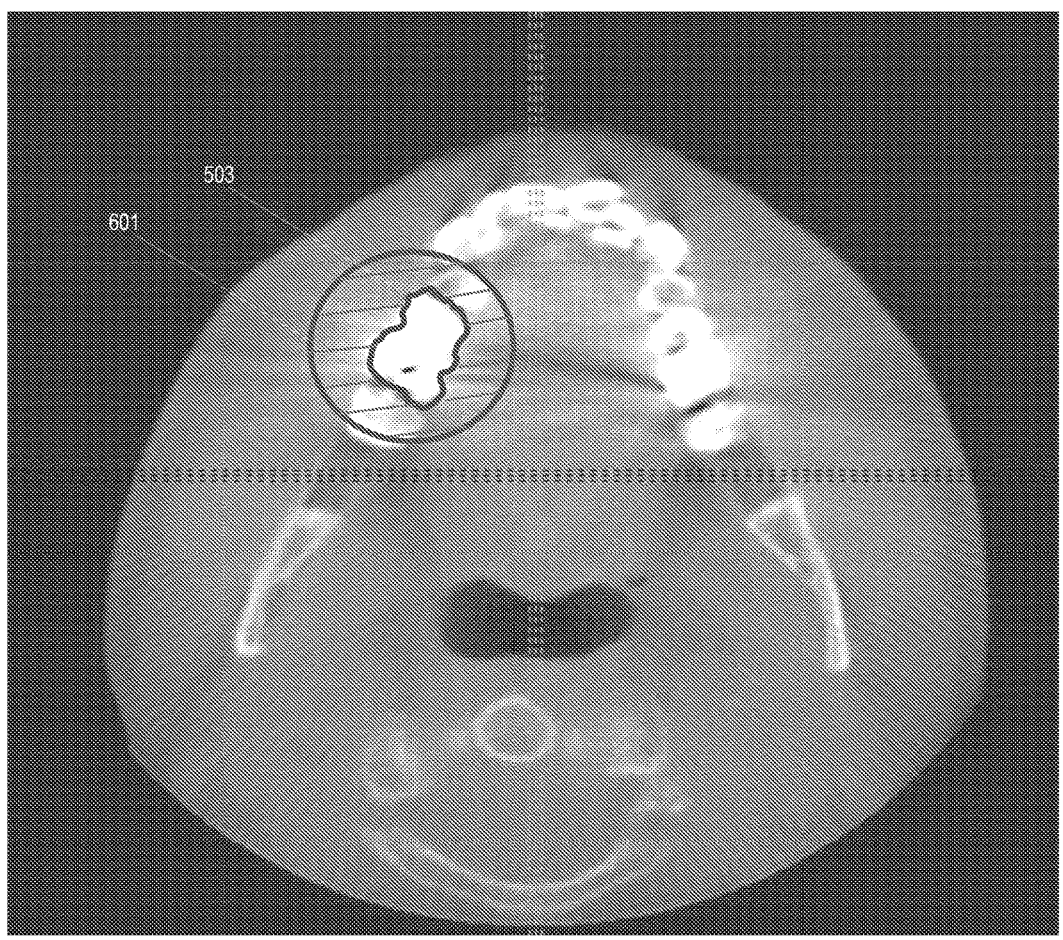
FIG. 8 is an image of a planar silhouette from the surface model of FIG. 5 overlaid onto a slice of the CT data of FIG. 3.

FIG. 5 shows a single horizontal slice from the CT model of the patient's teeth. Artifacts 301 can be seen reflecting from structures in the patient's teeth 303. FIG. 6 shows the fully constructed CT model. Again, artifacts 301 are clearly visible extending from the patient's teeth 303. These artifacts 301 hide some of the surface details of the patient's teeth 303 in the CT model. FIG. 7 shows a portion of the surface model generated by the image processing system 105 based on the surface information captured by the surface scanning system 107. The image processing system isolates a horizontal cut plane 501 in the surface model. This cut plane 501 corresponds to the slice from the CT model illustrated in FIG. 5. Because the surface model does not contain any data points from within the patient's teeth, the cut plane data identifies a silhouette shape 503 that corresponds to the outer surface of the patient's tooth on a given horizontal plane. In FIG. 8, the silhouette shape 503 from the cut plane 501 is overlaid onto the same tooth in the slice from the CT model.

After the silhouette data 503 from the surface model is overlaid onto the corresponding tooth in a slice of the CT model, the image processing system 105 identifies data points in the CT model that extend beyond the silhouette 503 (step 211). If data is detected outside of the silhouette shape 503, the system determines whether this data is artifact data. In some embodiments, all data in the CT model that extends beyond the silhouette shape 503 is assumed to be or is identified as artifact data and is removed from the CT model. In other embodiments, the data outside of the silhouette 503 is processed by a filtering or interpolation algorithm. The interpolation algorithm detects picture elements in the data just outside of the silhouette shape 503 that have densities that are above a threshold. The algorithm then interpolates data for these identified, artifact-associated pixels (or data points) with data from adjacent pixels not associated with artifact. FIG. 8 illustrates an area 601 just outside of the silhouette shape 503 that is to be analyzed by such a filtering algorithm.

After the CT data outside of the silhouette shape 503 has been interpolated, adjusted, or removed, the image processing system 105 moves onto another tooth in the same slice of CT data. After the necessary corrections have been made for each tooth, the image processing system 105 moves to another slice of CT data. This process repeats until all of the teeth in each of the CT data slices have been analyzed and the artifact data has been removed.

Figure 9:
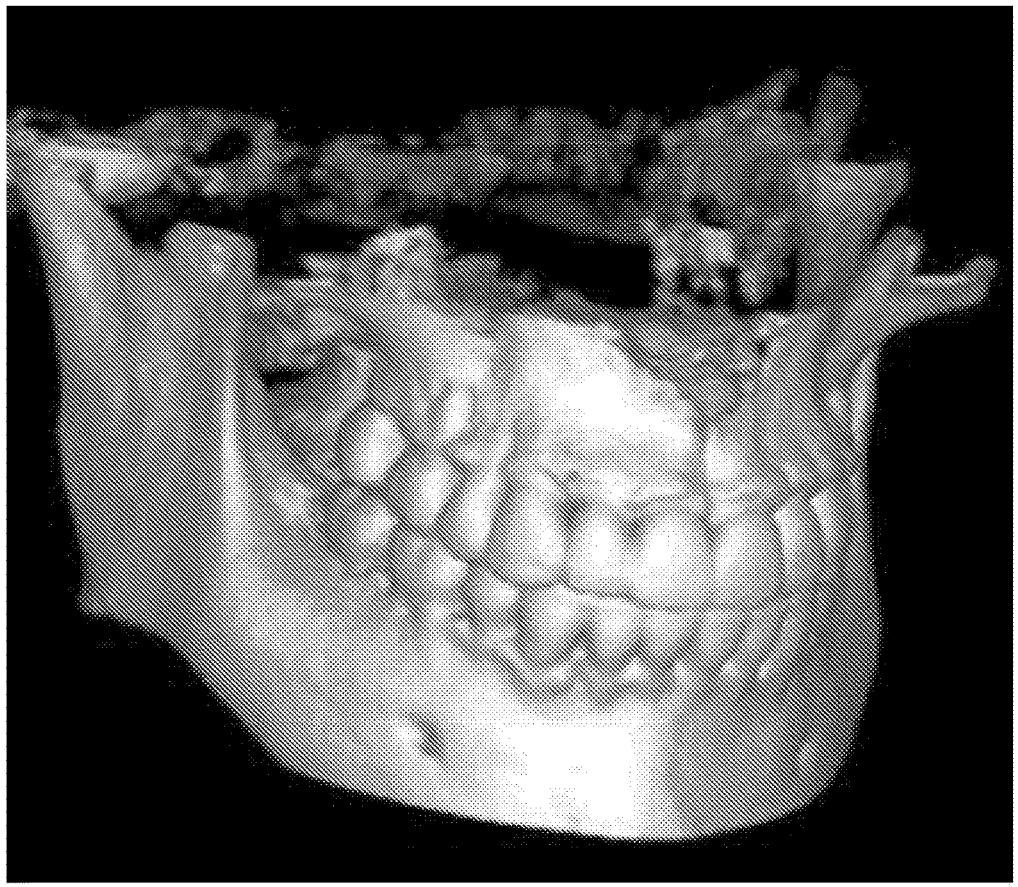
FIG. 9 is a perspective view of the CT model of FIG. 4 with the imaging artifacts removed.

After the CT data has been analyzed and the artifacts have been identified and removed, the image processing system 105 removes the overlaid surface model and any silhouette shapes from the CT data (step 213) and generates an artifact-reduced CT model. As pictured in FIG. 9, the artifacts have been removed from the artifact-reduced CT model and the surface of each tooth is visible.

Figure 3:
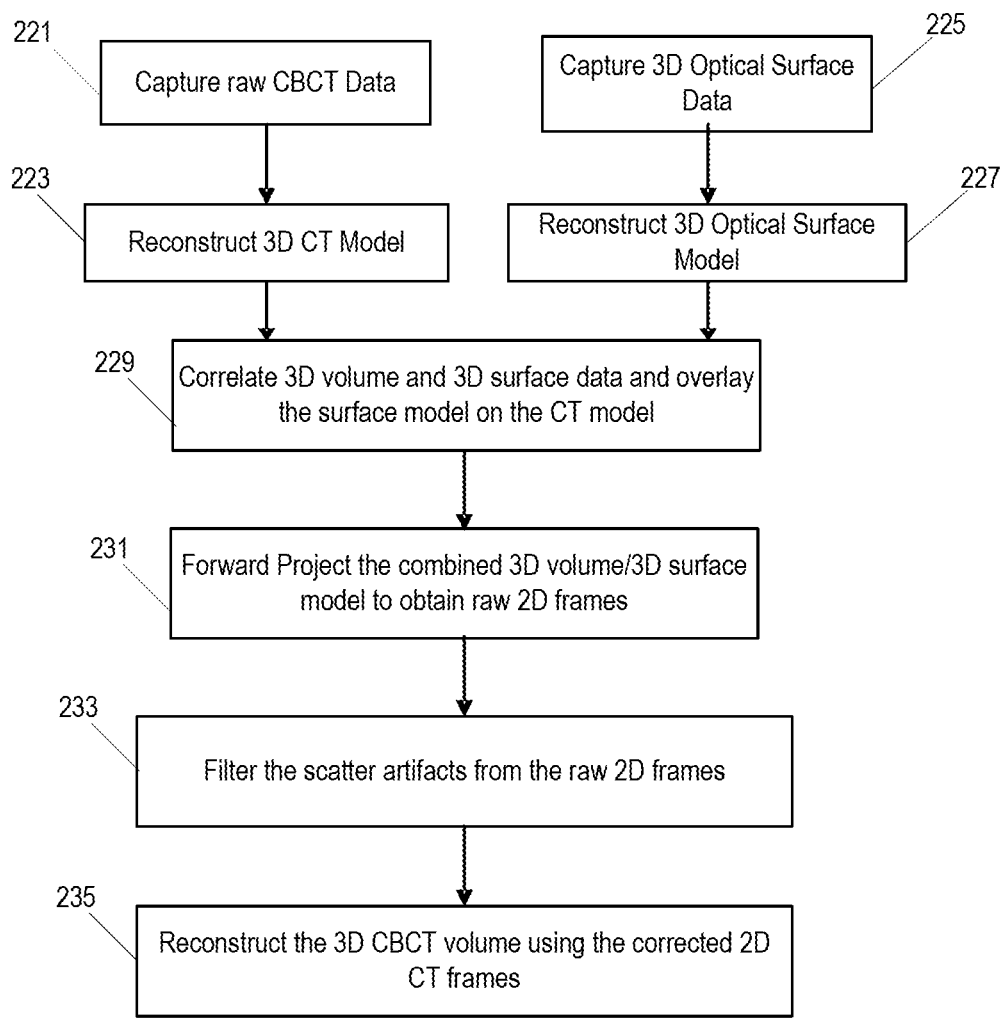
FIG. 3 is a flowchart showing a second method of using the system of FIG. 1A to remove artifacts from a CT model.

An alternative approach for combining the CT and optically derived surface data as presented in FIG. 3. As in the method of FIG. 2 above, the CT and optical data are both captured (steps 221, 225) and are both processed to produce 3D volumetric data (steps 223, 227). The data models are again correlated and overlaid (step 229). Once correlated, the two volumetric datasets in the combined data set are then both forward-projected in order to create a set of two-dimensional projection images (step 231). Optically-derived data is then used to identify the teeth surface and filter or compensate for the artifact-causing elements (created by scatter and beam hardening associated with metal in the image volume) in the images or frames that lead to artifacts in the reconstructed images (step 233). The filtering process removes artifacts before a three-dimensional model is reconstructed from the two-dimensional projection images (step 235).

Figure 4:
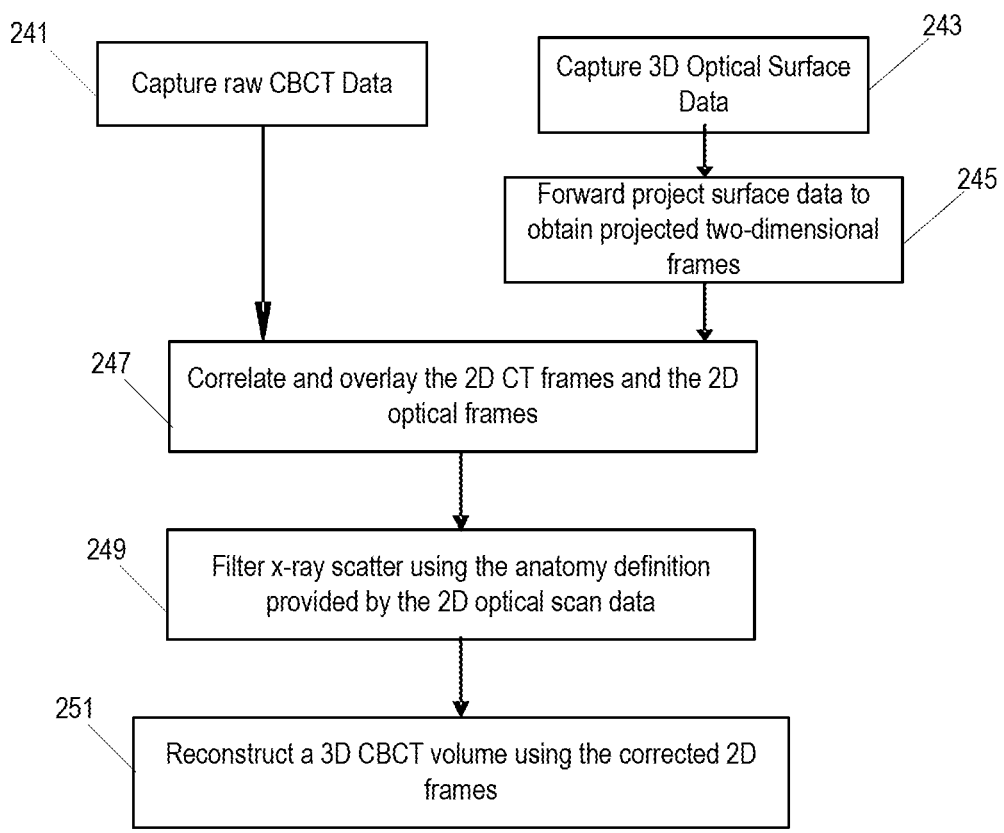
FIG. 4 is a flowchart showing a third method of using the system of FIG. 1A to remove artifacts from a CT model.

A third approach to combining the CT and optically-derived surface data is presented in FIG. 4. In this case, the CT and optical data are both captured as described above (steps 241, 243). However, instead of generating two three-dimensional models, the optical surface data is forward projected to generate two-dimensional projection images (step 245). The two dimensional images from the CT data and the two-dimensional projection images are correlated and overlaid (step 247). Artifact-causing elements that lead to artifacts in the reconstructed images are filtered from the raw CT data using the anatomy defined by the two-dimensional optical frames (step 249). A three-dimensional CT model is then constructed from the filtered and corrected CT data frames.

Figure 10:
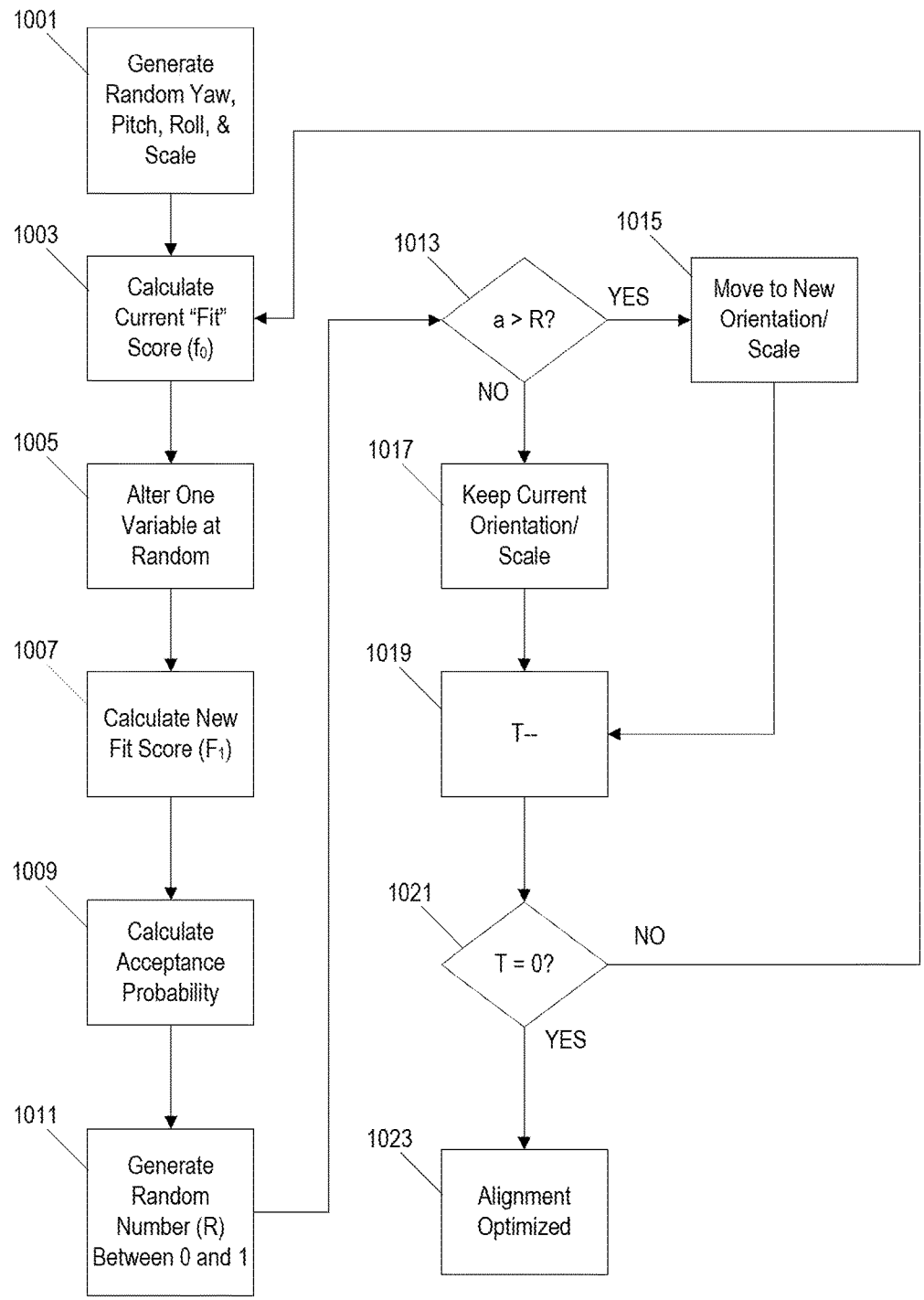
FIG. 10 is a flowchart of a method for determining an optimized alignment of a surface model and a CT model.

As discussed above, in some implementations, the system is configured to automatically determine a proper orientation and scale to correlate the surface model and the CT model. FIG. 10 illustrates an example of a method for automatically determining an optimized alignment of the two different models. According to the technique of FIG. 10, the scale and orientation of one of the models (e.g., either the CT model or the surface model) remains stationary throughout the optimization process. The yaw, pitch, roll, and scale of the other model is repeatedly adjusted until an optimized fit is determined. In this example, the CT model will remain stationary while the yaw, pitch, roll, and scale of the surface model is repeatedly adjusted.

First, a set of random yaw, pitch, roll, and scale values are generated for the surface model (step 1001). The center of the surface model sized and oriented according to the random values is aligned with the center of the CT model and a "fit" score ($F_0$) is calculated (step 1003). The "fit" score quantifies the degree to which the surface model aligns with the CT model. For example, it can be a score calculated based on the distance between each point on the surface model and the nearest "surface" point on the CT model. The "fit" score does not need to be capable of indicating when perfect alignment has been achieved—instead, it only need be capable of indicating when one orientation/scale presents a better "fit" than another.

After the current fit score ($F_0$) is calculated, one of the four orientation/scale variables is selected at random and altered by a fixed amount (step 1005). For example, if "roll" is randomly selected, the "roll" value is altered while the pitch, yaw, and scale values remain the same. A new "fit" score ($F_1$) is calculated based on the updated orientation/scale using the same formula as was used to calculate the "current fit score" ($F_0$) (step 1007).

Next, an acceptance probability is calculated based on the current fit score ($F_0$), the new fit score ($F_1$), and a T value (step 1009). As discussed further below, the T value begins at a relatively high value and is regularly decremented with each loop of the optimization routine illustrated in FIG. 10.

In some implementations, the acceptance probability value is calculated according to the equation:

$$a = e^{\frac{F_1 - F_0}{T}}$$

As such, if the new fit score ($F_1$) is better than the current fit score ($F_0$), the acceptance probability will be greater than one (1). However, if the new fit score is less than the current fit score, the acceptance probability will be less than one and will increasingly approach zero as the current fit score worsens. Similarly, as discussed in further detail below, the acceptance probability also increasingly approaches zero as the value of T decreases with each iteration.

After the acceptance probability (a) is calculated, a random number (R) between zero and one is generated (step 1011) and the acceptance probability (a) is compared to the random number (R) (step 1013). If the acceptance probability (a) exceeds the random number (R), then the optimization routine accepts the new randomly altered orientation/scale of the surface model (step 1015). Otherwise, the random alteration is rejected (step 1017) and the orientation/scale of the surface model remains as it was before the random alteration (in step 1005).

After the orientation/scale alteration is evaluated, the value of T is decreased (step 1019) and as long as T is not yet less than or equal to zero (step 1021), the optimization routine proceeds to execute another loop by calculating a current fit score (step 1003) and altering one of the four variables (i.e., yaw, pitch, roll, or scale) at random (step 1005). However, if T is less than or equal to zero after the decrease (step 1021), then the optimization routine is complete and the current orientation and scale of the surface model is deemed to be optimally aligned with the CT model (step 1023).

The optimization routine of FIG. 10 is based on the concept of simulated annealing. The routine of FIG. 10 randomly tests small alterations of the orientation/scale of the surface model to see if the "fit" can be improved. If the small alteration would improve the fit, the routine will always accept the fit (i.e., because the acceptance probability will be greater than one and the random number generated in step 1011 must be equal to or less than one). However, in order to avoid becoming stuck on a local maxima of a fit score, the mechanism of FIG. 10 will also sometimes accept an alteration that results in a worse fit score (as long as the calculated acceptance probability (step 1009) is greater than the random number generated in step 1011). As a result, the alignment optimization technique can move beyond a "local" optimized solution and locate an even better alignment. However, because the value T is decreased with each iteration of the optimization loop, the acceptance probability (step 1009) calculated for a move to an orientation/alignment that results in a worse fit score will become increasingly smaller each time the loop routine executes. As a result, although the optimization routine may be more willing to accept a move to a less optimal orientation/scale early in the optimization process, it will be increasingly less likely to accept a worse orientation/scale solution as the optimization routine progresses. By the time T approaches zero, the optimization routine is unlikely to change the orientation/scale of the surface model unless such a move would result in an improved "fit score."

Thus, the invention provides, among other things, a system for capturing CT data, generating a CT model, and removing artifacts from the generated CT model by capturing surface scan data of the patient's teeth, overlaying the surface scan data onto the CT model, and identifying, reducing, and removing artifacts that are outside of the surface scan data. Various features and advantages are set forth in the following claims.

What is claimed is:

1. A system for removing artifacts caused by x-ray reflective materials from an x-ray image, the system comprising:
   an x-ray source;
   an x-ray detector that captures x-ray images including a structure;
   an imaging device that captures a surface scan of the structure; and
   an image processor that constructs a three-dimensional CT model including the structure from the x-ray images and a three-dimensional surface model including the structure from the surface scan, the image processor resizing and orienting at least one of the surface model and the CT model so that the surface model and the CT model are of a same scale and orientation,
   overlaying the surface model on the CT model to generate a combined data set,
   detecting data points in the combined data set that extend beyond a surface of the structure in the surface model, wherein the detected data points represent artifacts in the CT model,
   adjusting the detected data points from the CT model by interpolation of the detected data points to create an artifact-reduced CT model, and
   displaying the artifact-reduced CT model.

2. The system of claim 1, wherein the imaging device includes a laser scanning system.

3. The system of claim 1, wherein the imaging device includes a structured light scanning system.

* * * * *